(12) United States Patent
Ji et al.

(10) Patent No.: US 11,583,242 B2
(45) Date of Patent: Feb. 21, 2023

(54) SYSTEM AND METHOD FOR CONTRAST ENHANCED ULTRASOUND QUANTIFICATION IMAGING

(71) Applicant: SHENZHEN MINDRAY BIO-MEDICAL ELECTRONICS CO., LTD., Guangdong (CN)

(72) Inventors: Ting-Ian Ji, San Jose, CA (US); Zhaoling Lu, San Jose, CA (US)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 61 days.

(21) Appl. No.: 17/062,438

(22) Filed: Oct. 2, 2020

(65) Prior Publication Data

US 2022/0104788 A1 Apr. 7, 2022

(51) Int. Cl.
- *A61B 8/00* (2006.01)
- *A61B 8/06* (2006.01)
- *A61B 8/08* (2006.01)

(52) U.S. Cl.
CPC ............. *A61B 8/06* (2013.01); *A61B 8/461* (2013.01); *A61B 8/481* (2013.01); *A61B 8/54* (2013.01)

(58) Field of Classification Search
CPC ........... A61B 8/06; A61B 8/461; A61B 8/481; A61B 8/54; A61B 8/5223
See application file for complete search history.

(56) References Cited

U.S. PATENT DOCUMENTS

| | | | |
|---|---|---|---|
| 2009/0028406 A1* | 1/2009 | Arditi | A61B 8/06 382/131 |
| 2011/0213244 A1* | 9/2011 | Frinking | G01R 33/56366 600/431 |
| 2013/0190600 A1* | 7/2013 | Gupta | A61B 8/0866 600/410 |
| 2015/0196281 A1* | 7/2015 | Takagi | A61B 8/5223 600/408 |
| 2020/0357117 A1* | 11/2020 | Lyman | A61B 6/5205 |

* cited by examiner

Primary Examiner — Yi-Shan Yang
Assistant Examiner — Alexei Bykhovski
(74) Attorney, Agent, or Firm — Sheppard Mullin Richter & Hampton LLP

(57) ABSTRACT

Methods, systems, and apparatus, including computer programs encoded on computer storage media, for contrast enhanced ultrasound quantification imaging are provided. One of the methods includes: obtaining, for each location in a region of interest, a time-dependent ultrasound signal with respect to the region of interest for a time period; determining, for the each location, a processed time-dependent ultrasound signal based at least on the obtained time-dependent ultrasound signal, wherein: the processed time-dependent ultrasound signal maps one or more portions of the obtained time-dependent ultrasound signal that each locally increase over a threshold, and the processed time-dependent ultrasound signal flattens one or more portions of the obtained time-dependent ultrasound signal that do not each locally increase over the threshold; and generating a sequence of images of the region of interest based at least on the processed time-dependent ultrasound signal of the each location, wherein the generated sequence of images displays signal variations of the processed time-dependent ultrasound signal in one or more structures in the region of interest to render the one or more structures.

20 Claims, 7 Drawing Sheets

SYSTEM AND METHOD FOR CONTRAST ENHANCED ULTRASOUND QUANTIFICATION IMAGING

TECHNICAL FIELD

The disclosure relates generally to contrast enhanced ultrasound quantification imaging, and in particular to methods and systems for visualization of blood flow direction and distribution in vascular structures.

BACKGROUND

Ultrasound imaging is a non-invasive medical test for examining soft tissues (e.g., blood vessels) within bodies to show the structural details of internal tissues and fluid flow. Many ultrasound imaging systems utilize injectable ultrasound contrast agents to achieve high-contrast images, which are desirable for visualizing blood flow in organic structures inside the bodies. For example, images of blood flow direction and distribution usually help physicians diagnose and treat medical conditions.

Measuring and imaging fluid flow (e.g., blood flow) within the bodies is typically done using a Doppler ultrasound, which is an imaging test that shows blood moving through blood vessels. In Doppler ultrasound, the blood flow may be displayed based on the frequency reflected from moving blood cells, which may correspond to the velocity in the fluid flow. However, slow low-volume blood flow, e.g., in the capillaries, may not be demonstrated with conventional Doppler methods, and thus, the Doppler ultrasound may not be able to visualize different vascular structures (e.g., different sizes of blood vessels) in the region of interest. Furthermore, the Doppler ultrasound may not be used to demonstrate the organic structures, for example, to visualize blood flow distribution and perfusion in the region of interest. Thus, there is a need to non-invasively image blood flow direction and distribution of different blood vessels, and also provide important parameters such as blood flow perfusion in vascular structures.

SUMMARY

Various embodiments of the specification include, but are not limited to, systems, methods, and non-transitory computer readable media for contrast enhanced ultrasound quantification imaging.

In some embodiments, a non-transitory computer-readable storage medium for contrast enhanced ultrasound quantification imaging is configured with instructions executable by one or more processors to cause the one or more processors to perform operations comprising: obtaining, for each location in a region of interest, a time-dependent ultrasound signal with respect to the region of interest for a time period; determining, for the each location, a processed time-dependent ultrasound signal based at least on the obtained time-dependent ultrasound signal, wherein the processed time-dependent ultrasound signal maps one or more portions of the obtained time-dependent ultrasound signal that each locally increase over a threshold, and the processed time-dependent ultrasound signal flattens one or more portions of the obtained time-dependent ultrasound signal that do not each locally increase over the threshold; and generating a sequence of images of the region of interest based at least on the processed time-dependent ultrasound signal of the each location, wherein the generated sequence of images displays signal variations of the processed time-dependent ultrasound signal in one or more structures in the region of interest to render the one or more structures.

In some embodiments, the generated sequence of images display a wash-in process of agent-carrying blood perfusing through one or more vascular structures in the region of interest.

In some embodiments, the processed time-dependent ultrasound signal is a monotonically increasing signal.

In some embodiments, the obtained time-dependent ultrasound signal comprises an obtained time-dependent ultrasound intensity signal in a series of time frames from a first to a last time frame according to progression of time; and the processed time-dependent ultrasound signal comprises a processed ultrasound intensity signal in the series of time frames.

In some embodiments, determining, for the each location, the processed time-dependent ultrasound signal based at least on the obtained time-dependent ultrasound signal comprises, for the each location performing: for the first time frame, mapping the obtained time-dependent ultrasound intensity signal to the processed time-dependent intensity ultrasound signal, and iteratively for each of the series of time frames after the first time frame; and determining whether a current ultrasound intensity signal in a current time frame of the obtained time-dependent ultrasound intensity signal exceeds a previous ultrasound intensity signal in a previous time frame of the processed time-dependent ultrasound intensity signal for over the threshold: in response to the current ultrasound intensity signal in the current time frame of the obtained time-dependent ultrasound intensity signal exceeding the previous ultrasound intensity signal in the previous time frame of the processed time-dependent ultrasound intensity signal for over the threshold, mapping the current ultrasound intensity signal in the current time frame of the obtained time-dependent ultrasound intensity signal to a current intensity signal in the current time frame of the processed time-dependent ultrasound intensity signal, and in response to the current ultrasound intensity signal in the current time frame of the obtained time-dependent ultrasound intensity signal not exceeding the previous ultrasound intensity signal in the previous time frame of the processed time-dependent ultrasound intensity signal for over the threshold, mapping the previous ultrasound intensity signal in the previous time frame of the processed time-dependent ultrasound intensity signal to the current intensity signal in the current time frame of the processed time-dependent ultrasound intensity signal.

In some embodiments, generating the sequence of images of the region of interest based at least on the processed time-dependent ultrasound signal of the each location comprises: obtaining a starting time frame and an ending time frame; and generating the sequence of images between the starting time frame and the ending time frame.

In some embodiments, the operations further comprise: obtaining an updated starting time frame or an updated ending time frame; and correspondingly updating the generated sequence of images based at least on the updated starting time frame or the updated ending time frame.

In some embodiments, the operations further comprise: obtaining a user-controllable display speed; and displaying the generated sequence of images based at least on the obtained user-controllable display speed.

In some embodiments, before generating the sequence of images, the operations further comprise: comparing a predetermined time-dependent ultrasound signal and the processed time-dependent ultrasound signal; and determining, based at least on the comparison, one or more locations showing abnormality, wherein: the generated sequence of images comprise one or more labels indicating the one or more locations showing abnormality.

In some embodiments, a system for contrast enhanced ultrasound quantification imaging comprises one or more processors and one or more non-transitory computer-readable memories coupled to the one or more processors and configured with instructions executable by the one or more processors to cause the one or more processors to perform operations comprising: obtaining, for each location in a region of interest, a time-dependent ultrasound signal with respect to the region of interest for a time period; determining, for the each location, a processed time-dependent ultrasound signal based at least on the obtained time-dependent ultrasound signal, wherein the processed time-dependent ultrasound signal maps one or more portions of the obtained time-dependent ultrasound signal that each locally increase over a threshold, and the processed time-dependent ultrasound signal flattens one or more portions of the obtained time-dependent ultrasound signal that do not each locally increase over the threshold; and generating a sequence of images of the region of interest based at least on the processed time-dependent ultrasound signal of the each location, wherein the generated sequence of images displays signal variations of the processed time-dependent ultrasound signal in one or more structures in the region of interest to render the one or more structures.

In some embodiments, a method for contrast enhanced ultrasound quantification imagining comprises: obtaining, for each location in a region of interest, a time-dependent ultrasound signal with respect to the region of interest; and generating a sequence of images of the region of interest based on the time-dependent ultrasound signal of the each location, wherein the generated sequence of images displays signal variations from a starting frame to an ending frame, and, in the generated sequence of images, for the each location, when the time-dependent ultrasound signal reaches a peak value, the peak value is held from a time frame corresponding to the peak value to the ending time frame. In some embodiments, the method further comprises: displaying, for the each location in the region of interest, the peak value of the time-dependent ultrasound signal in the image at the ending time frame of the generated sequence.

In some embodiments, a method for contrast enhanced ultrasound quantification imaging comprises: obtaining, for each location in a region of interest, a time-dependent ultrasound signal with respect to the region of interest for a time period; determining, for the each location, a processed time-dependent ultrasound signal based at least on the obtained time-dependent ultrasound signal, wherein the processed time-dependent ultrasound signal maps one or more portions of the obtained time-dependent ultrasound signal that each locally increase over a threshold, and the processed time-dependent ultrasound signal flattens one or more portions of the obtained time-dependent ultrasound signal that do not each locally increase over the threshold; and generating a sequence of images of the region of interest based at least on the processed time-dependent ultrasound signal of the each location, wherein the generated sequence of images displays signal variations of the processed time-dependent ultrasound signal in one or more structures in the region of interest to render the one or more structures.

In some embodiments, a system for contrast enhanced ultrasound quantification imaging comprises: an ultrasound transducer configured to emit and receive ultrasound waves reflected from a region of interest and generate ultrasound signals based on the received ultrasound waves; and a computing system comprising: one or more processors, and one or more non-transitory computer-readable storage media coupled to the one or more processors and having instructions stored thereon that are executable by the one or more processors to cause the one or more processors to perform operations. The operations comprise: obtaining, for each location in a region of interest, a time-dependent ultrasound signal with respect to the region of interest for a time period from the generated ultrasound signals; determining, for the each location, a processed time-dependent ultrasound signal based at least on the obtained time-dependent ultrasound signal, wherein the processed time-dependent ultrasound signal maps one or more portions of the obtained time-dependent ultrasound signal that each locally increase over a threshold, and the processed time-dependent ultrasound signal flattens one or more portions of the obtained time-dependent ultrasound signal that do not each locally increase over the threshold; and generating a sequence of images of the region of interest based at least on the processed time-dependent ultrasound signal of the each location, wherein the generated sequence of images displays signal variations of the processed time-dependent ultrasound signal in one or more structures in the region of interest to render the one or more structures.

Embodiments disclosed herein have one or more technical effects. In some embodiments, the methods and systems may provide visualization of blood flow direction and distribution in various biological structures, including tissues or vascular structures, in a region of interest. For example, the generated sequence of images may provide visualization of the direction and the distribution of the blood flow of vascular structures, such as blood vessels of different sizes, based on the processed ultrasound signals. In some embodiments, the methods and systems may further measure relative blood flow velocities of different vascular structures based on the generated sequence of images in the region of interest. It allows a user to compare blood perfusion in the various biological structures. In some embodiments, the blood flow distribution provides information in diagnosis and treatment of vascular malformation based on the processed ultrasound signals. For example, a computer may compare the generated sequence of images with a baseline (e.g., flow rate data or tissue image for a health body), and based on the comparison, pinpoint on the locations or nearby locations of the generated sequence of images (e.g., at the tissue level) causing health issues.

These and other features of the systems, methods, and non-transitory computer readable media disclosed herein, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for purposes of illustration and description only and are not intended as a definition of the limits of the invention. It is to be understood that the foregoing general description and the following detailed description are exemplary and explanatory only, and are not restrictive of the invention, as claimed.

DETAILED DESCRIPTION

Figure 1:
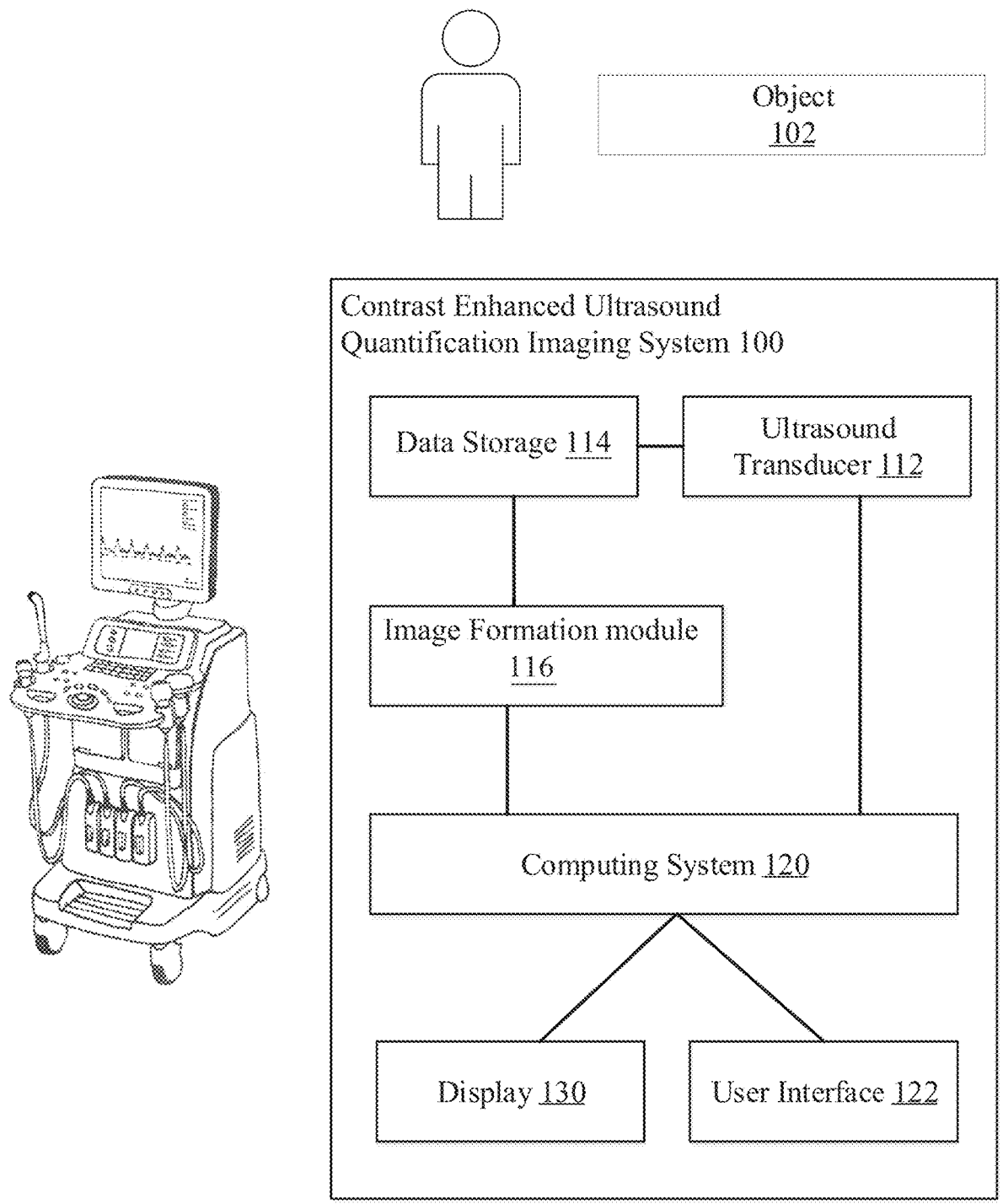
FIG. 1 illustrates an exemplary environment of contrast enhanced ultrasound quantification imaging system, in accordance with various embodiments.

FIG. 1 illustrates an exemplary environment of contrast enhanced ultrasound quantification imaging (CEUS QI) system 100 for contrast enhanced ultrasound quantification imaging, in accordance with various embodiments. Depending on the implementation, the CEUS QI system 100 may include additional, fewer, or alternative components.

In some embodiments, the CEUS QI system 100 may include an ultrasound transducer 112, a data storage 114, an image formation module 116, a computing system 120, a user interface 122, and a display 130, one or more of which may be optional. The ultrasound transducer 112 may couple to the data storage 114 and the computing system 120, the data storage 114 may couple to the image formation module 116, the image formation module 116 may couple to the computing system 120, and the computing system 120 may couple to the display 130 and the user interface 122. Any coupled modules may transmit signals between each other. The ultrasound transducer 112, the data storage 114, the image formation module 116, the computing system 120, the user interface 122, and the display 130 may be integrated in a single system or device or be distributed in several connected systems or devices.

In some embodiments, an object 102 (e.g., a human, a pet, a tissue section, a live sample) may be prepared for CEU QI with respect to a region of interest (ROI), such as belly, heart, etc. For example, a human may be injected with a contrast agent through vascular injection, after which the ROI may be exposed to ultrasound waves. In one embodiment, the computing system 120 may trigger the ultrasound transducer 112 to emit ultrasound waves towards the ROI. For example, the ultrasound transducer may be placed on a patient's body, allowing ultrasound waves to emit towards the ROI on the body. The ROI may contain skin, nail, hair, or the like of a body surface, under which various organic structures (e.g., tissue, blood vessel) may reflect back the ultrasound waves in various degrees. In one embodiment, there may be a plurality of different blood vessels such as arteries, veins, and capillaries of various sizes in the ROI. In some embodiments, the ultrasound transducer 112 may include a detector. The detector may be configured to receive ultrasound waves reflected from the ROI and generate ultrasound signals based on the received ultrasound waves. For example, the detector may convert the reflected ultrasound waves into the electrical signals to obtain ultrasound signals. In some embodiments, the ultrasound transducer 112 may send the ultrasound signals to the data storage 114. The data storage 114 may be configured to store the ultrasound signals generated from the ultrasound transducer 112 and send to the image formation module 116. The image formation module 116 may be optional and configured to adjust the ultrasound signal amplitudes and phases, for example, by performing a delay for focus, weighting, channel summation, etc. Then, the image formation 116 may send the adjusted ultrasound signals to the computing system 120 to undergo related signal processes The computing system 120 may be a system for CEUS QI. The signal process for the CEUS QI is described below with respect to FIG. 2.

In some embodiments, depending on different imaging modes requested through the user interface 122, the computing system 120 may perform different processes on the ultrasound signals to generate corresponding images. For example, the intensity of the ultrasound signals and intensity variations for each location in the ROI may be recorded for the time period to generate the images. The generated images may be displayed on the display 130 to the user. Through the user interface 122, the user may update request configurations or otherwise input instructions to modify the images, for example, changing display modes.

Figure 2:
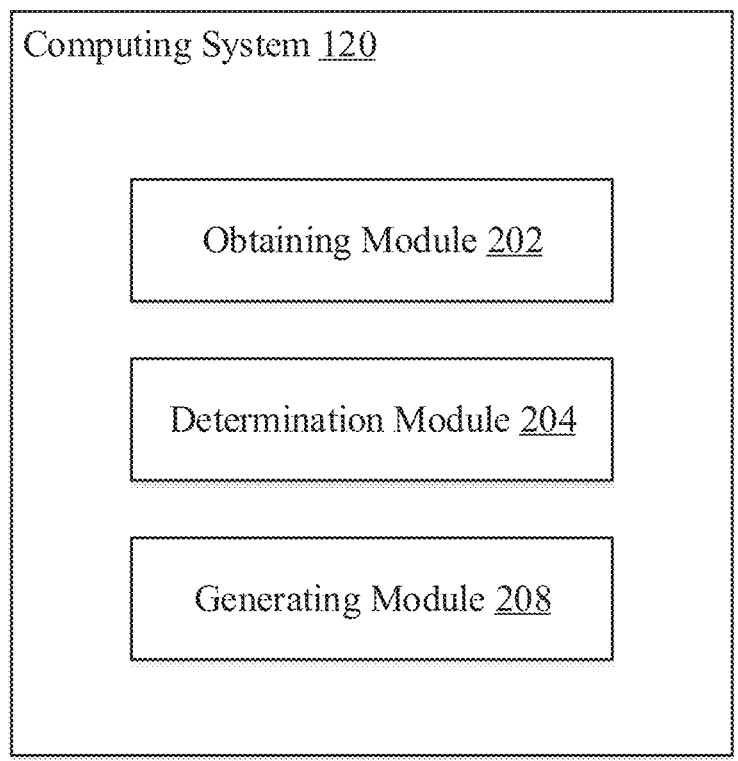
FIG. 2 illustrates an exemplary computing system for contrast enhanced ultrasound quantification imaging, in accordance with various embodiments.

FIG. 2 illustrates an exemplary computing system 120 for CEUS QI, in accordance with various embodiments. Depending on the implementation, the computing system 120 may include additional, fewer, or alternative components.

The computing system 120 for CEUS QI may include one or more processors (e.g., a digital processor, an analog processor, a digital circuit designed to process information, a central processing unit, a graphics processing unit, a microcontroller or microprocessor, an analog circuit designed to process information, a state machine, and/or other mechanisms for electronically processing information) and one or more non-transitory computer-readable memories (e.g., permanent memory, temporary memory, non-transitory computer-readable storage medium) coupled to each other. The one or more memories may be configured with instructions executable by the one or more processors. The processor(s) may be configured to perform various operations by interpreting machine-readable instructions stored in the memories. The computing system 120 may include other computing resources. The computing system 120 may be installed with appropriate software (e.g., ultrasound imaging control program) and/or hardware (e.g., wires, wireless connections) to access other computing resources.

The computing system 120 for CEUS QI may also include an obtaining module 202, a determination module 204, and a generating module 206. That is, the obtaining module 202, the determination module 204, and the generating module 206 may be implemented as software (e.g., a part of software instructions), as hardware, or as a combination of software and hardware. As software instructions, the various modules may be executed by the one or more processors of the computing system 120 to perform various operations.

While the computing system 120 for CEUS QI is shown in FIG. 2 as a single entity, this is merely for ease of reference and is not meant to be limiting. One or more of the modules or one or more functionalities of the computing system 120 described herein may be implemented in a single computing device or distributed in multiple computing devices. In some embodiments, one or more of the modules or one or more functionalities of the computing system 120 described herein may be implemented in one or more networks (e.g., an enterprise network accessible to an ultrasound machine), one or more endpoints (e.g., in an ultrasound machine), one or more servers (e.g., a server connected to an ultrasound machine), one or more clouds (e.g., a could accessible to an ultrasound machine), etc.

The obtaining module 202 may be configured to obtain, for each location of an ROI, a time-dependent ultrasound signal with respect to the ROI for a time period from CEUS images. The CEUS images for the time period may be generated based on intensity variations for the each location of the ROI, and stored in the computing system 120 for CEUS QI. Collectively for the entire ROI, the obtained information from the CEUS images may include ultrasound signals received for the time period. Obtaining information may include one or more of accessing, acquiring, analyzing, determining, examining, identifying, loading, locating, opening, receiving, retrieving, reviewing, storing, or otherwise obtaining the information. The ultrasound signal may be transmitted from the ultrasound transducer 112 or the image formation module 116 as described above, or otherwise obtained by the computing system 120. For the time-dependent ultrasound signal, the ultrasound signal may be obtained for the time period to capture time-dependent variations in intensity or one or more other parameters. The ROI may refer to a two-dimensional surface of any size (e.g., a body surface, a cross-section under a body surface), and the obtained ultrasound signal may be derived at least from ultrasound waves reflected by structures (e.g., blood vessels of different sizes, tissues between the blood vessels) at any depth below the surface. Alternatively, the ROI may refer to a three-dimensional space of any size (e.g., a volume under a body surface).

The CEUS QI may be performed while the contrast agent is injected and passes through the ROI. The CEUS images may be generated in real time based on the contrast enhanced ultrasound signals of each location of the ROI. For example, the intensity of the ultrasound signals and intensity variations for each location in the ROI may be recorded in real time to generate the CEUS images. In other words, the time-dependent ultrasound signal is generated and received in response to the injection of contrast agent to the patient and the corresponding CEUS images are generated and stored as the input to the CEUS QI system.

Figure 3:
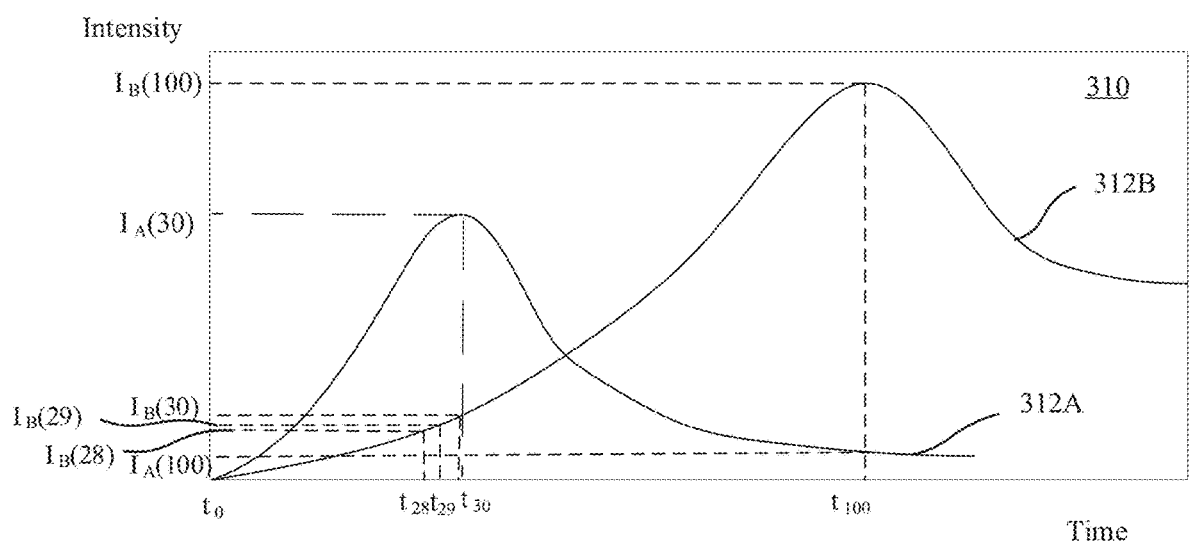
FIG. 3 illustrates an example diagram of time intensity curves of ultrasound signals, in accordance with various embodiments.

In some embodiments, before or after obtaining the time-dependent ultrasound signal, the computing system 120 (e.g., another obtaining module) may be configured to obtain a user-input to determine a starting time frame and an ending time frame. For example, the computing system 120 may obtain, through the user interface 122, the ending time frame. As another example, the computing system 120 may be configured to set the starting time frame and the ending time frame. The starting time frame may refer to a start of injection of the contrast agent. The ending time frame may refer to an end of the time period of the CEUS QI. For example, as shown in FIG. 3, the computing system 120 may be configured to determine a series of time frames between the $t_0$ (i.e., the starting time frame) and $t_{100}$ (i.e., the ending time frame). The obtained time-dependent ultrasound intensity signals may be transmitted to the determination module 204 for further processing.

The determination module 204 may be configured to determine, for the each location, a processed time-dependent ultrasound signal based at least on the obtained time-dependent ultrasound signal. The computing system 120 may be configured to process the obtained time-dependent ultrasound signal for a location based on a threshold. The threshold may be a parameter of intensity increment used for CEUS QI described below. For example, the computing system 120 may obtain the threshold through the user interface 122 (e.g., inputted by a user). As another example, the computing system 120 may be configured to set the threshold. The obtained threshold may be transmitted to the determination module 204 for further processing. The threshold may be adjustable in real time, which may cause the generated sequence of images to update in real time. The processed time-dependent ultrasound signal may map one or more portions of the obtained time-dependent ultrasound signal that locally increases over the threshold. That is, the processed ultrasound signal may be recorded to be the same as the obtained ultrasound signal. The processed time-dependent ultrasound signal may flatten one or more portions of the obtained time-dependent ultrasound signal that does not locally increase over the threshold. That is, the computing system 120 may replace the obtained ultrasound signal with the last processed ultrasound signal. In some embodiments, the processed time-dependent ultrasound signal is a monotonically increasing signal. That is, the processed time-dependent ultrasound signal may be always increasing or remaining constant, and may never be decreasing. The processed time-dependent ultrasound signal is described in more details with reference to FIG. 4A.

The obtained time-dependent ultrasound signal may comprise an obtained ultrasound intensity signal in a series of time frames from a first to a last time frame according to progression of time. The computing system 120 may be configured to obtain, for each location, an intensity signal of the obtained time-dependent ultrasound signal at each time frame. The obtained intensity signal may refer to a quantified value of the obtained ultrasound signal. The determination module 204 may be configured to determine, for the each location, a Time Intensity Curve (TIC) based at least on the obtained time-dependent ultrasound intensity signal for the time period. Referring now to FIG. 3, FIG. 3 illustrates time intensity curves of ultrasound signals 310, in accordance with various embodiments. For example, the determination module 204 may organize the obtained time-dependent ultrasound intensity signal of the location into the TIC. The TIC may depict the intensity variation of the ultrasound intensity signal for the period of time. In some embodiments, the determination module 204 may be configured to determine the obtained time-dependent ultrasound intensity signal for each location in each time frame in the series of time frames. For examples, as shown in FIG. 3, based on the obtained time-dependent ultrasound signal for locations A and B, the determination module 204 may determine the intensity variations of the corresponding ultrasound intensity signals in the series of time frames. The locations A and B may correspond to different spots on different structures within the ROI. As shown in diagram 310 in FIG. 3, the intensity variation for location A is represented by TIC 312A, and the intensity variation for location B is represented by TIC 312B. As shown, the TICs are plotted against an x-axis of frame time and an y-axis of signal intensity. The data points in the TICs may be fitted with smooth functions. In one example, location A and TIC 321A may correspond to a finer blood vessel (e.g., capillary), and location B and TIC 321B may correspond to a wider blood vessel (e.g., artery).

The processed time-dependent ultrasound signal may comprise a processed ultrasound intensity signal in the series of time frames. The processed time-dependent ultrasound intensity signal for the each of the series of time frames may be determined by an equation as follows:

$$I_{PH}(k)=p*I(k)+(1-p)*I_{PH}(k-1) \quad k=1,2,\ldots,K_N-1$$

where
$p=1$, if $I(k)-I_{PH}(k-1)>\Delta I_{TH}$
$=0$, if $I(k)-I_{PH}(k-1)\leq\Delta I_{TH}$ The component I(k) may be referred to as an ultrasound intensity signal in the kth time frame of the obtained time-dependent ultrasound intensity signal, the component $I_{PH}(k)$ may be referred to as an ultrasound intensity signal in the kth time frame of the processed time-dependent ultrasound intensity signal, the component $I_{PH}(k-1)$ may be referred to as a previous ultrasound intensity signal in the (k-1)th time frame of the processed time-dependent ultrasound intensity signal, and the component Atm may be referred to as a threshold intensity.

According to the equation, if $I(k)-I_{PH}(k-1)>\Delta I_{TH}$, that is, the ultrasound intensity signal in the kth time frame of the obtained ultrasound intensity signal exceeds the previous ultrasound intensity signal in the (k-1)th time frame of the processed ultrasound intensity signal for over $\Delta I_{TH}$, the computing system 120 may determine p=1, resulting in $I_{PH}(k)=I(k)$. Accordingly, the ultrasound intensity signal in the kth time frame of the processed ultrasound signal may be mapped to be the same as the one in the kth time frame of the obtained ultrasound intensity signal. On the other hand, if $I(k)-I_{PH}(k-1) \leq \Delta I_{TH}$, that is, the ultrasound intensity signal in the kth time frame of the obtained ultrasound intensity signal does not exceed the previous ultrasound intensity in the (k-1)th time frame of the processed ultrasound intensity signal for over $\Delta I_{TH}$, the computing system 120 may determine p=0, resulting in $I_{PH}(k)=I_{PH}(k-1)$. Accordingly, the ultrasound signal in the kth time frame of the processed ultrasound signal may be mapped to be the same as the previous ultrasound intensity signal in the (k-1)th time frame of the processed ultrasound signal.

The determination module 204 may be configured to map, for the first time frame, the obtained time-dependent ultrasound intensity signal to the processed time-dependent intensity ultrasound signal. For example, when the first time frame is determined to be 0, that is, at a time of injection of a contrast agent, the processed intensity ultrasound signal (i.e., $I_{PH}(0)$) may be recorded to be the same as the obtained ultrasound intensity signal (i.e., $I_{PH}(0)=I(0)$). The determination module 204 may further be configured to determine, iteratively for each of the series of time frames after the first time frame, whether a current ultrasound intensity signal in a current time frame of the obtained time-dependent ultrasound intensity signal exceeds a previous ultrasound intensity signal in a previous time frame of the processed time-dependent ultrasound intensity signal for over the threshold.

Figure 4A:
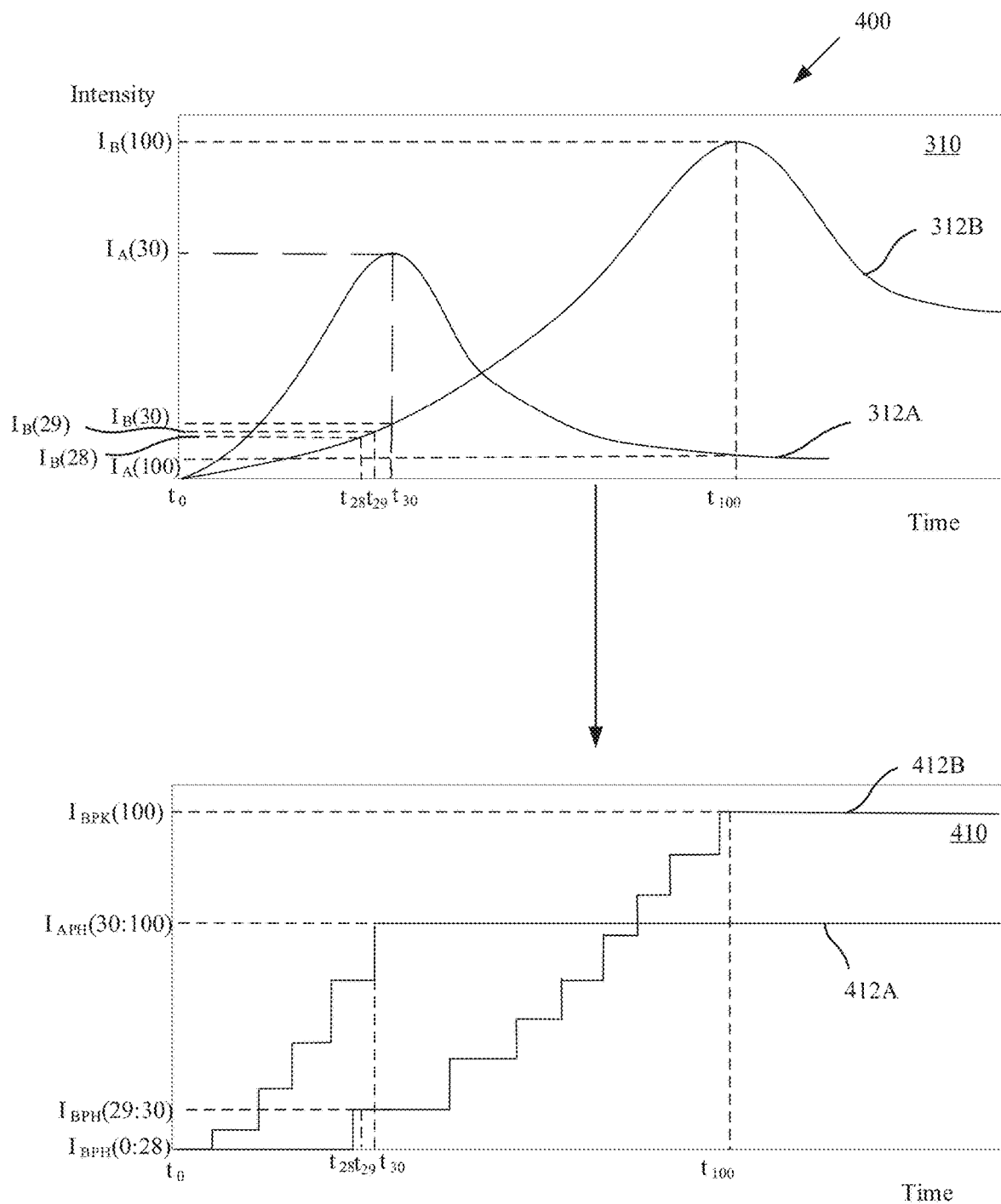
FIGS. 4A-4B illustrate exemplary work flows of a determination module and a generating module, in accordance with various embodiments.

Referring to FIG. 4A, FIG. 4A illustrates an exemplary work flow 400 of the determination module 206, in accordance with various embodiments. As shown in FIG. 4A, diagram 310 may refer to intensity variations for locations A and B based on the obtained time-dependent ultrasound intensity signal, and the intensity value of the obtained ultrasound signal at locations A and B are determined based on the TICs 312A and 312B. Diagram 410 may refer to intensity variations for the locations A and B based on the processed time-dependent ultrasound intensity signal, and the intensity value of the processed time-dependent ultrasound intensity signal at the locations A and B are determined based on the monotonically increasing curves 412A and 412B. The determination module 204 may be configured to determine processed ultrasound intensity signal for different locations based on the obtained ultrasound intensity signal. For example, the intensity signal at time frame $t_{100}$ for the locations A and B may be determined to be $I_A(100)$ and $I_B(100)$ respectively. At the same time frame $t_{100}$, the processed ultrasound signal for the locations A and B may be determined to be $I_{APH}(30:100)$ and $I_{BPH}(100)$ respectively based on the monotonically increasing curves 412A and 412B. Since the contrast agent reaches different locations at different times based on sizes of vascular structures and/or distance from the injection spot, the contrast enhancement in different locations may vary, and the intensity signals for each locations at the same time frame may be different.

The determination module 204 may map, in response to the current ultrasound intensity signal in a current time frame of the obtained time-dependent ultrasound intensity signal exceeding the previous ultrasound intensity signal in the previous time frame of the processed time-dependent ultrasound intensity signal for over the threshold, the current ultrasound intensity signal in the current time frame of the obtained time-dependent ultrasound intensity signal to a current intensity signal in the current time frame of the processed time-dependent ultrasound intensity signal. For example, as shown in the diagram 310, for the location B, since the current intensity signal at the time frame $t_{29}$ of the obtained ultrasound intensity signal (e.g., $I_B(29)$ in the diagram 310) exceeds the previous intensity signal in the previous time frame (i.e., $t_{28}$) of the processed ultrasound intensity signal (i.e., $I_{BPH}(0:28)$ in the diagram 410) over a threshold, the determination module may be configured to map $I_B(29)$ to the intensity signal in the time frame $t_{29}$ of the processed ultrasound intensity signal (i.e., $I_B(29)=I_{BPH}(29)$ at $t_{29}$).

In some embodiments, the determination module 204 may, in response to the current ultrasound intensity signal in the current time frame of the obtained time-dependent ultrasound intensity signal not exceeding the previous ultrasound intensity signal in the previous time frame of the processed time-dependent ultrasound intensity signal for over the threshold, map the previous ultrasound intensity signal in the previous time frame of the processed time-dependent ultrasound intensity signal for over the threshold to the current intensity signal in the current time frame of the processed time-dependent ultrasound intensity signal. For example, for the same location B, since the intensity signal at the time frame $t_{30}$ of the obtained ultrasound intensity signal (e.g., $I_B(30)$ in the diagram 310) does not exceed the previous intensity signal in the previous time frame (i.e. $t_{29}$) of the processed ultrasound intensity signal (i.e., $I_{BPH}(29)$ in the diagram 410) over the threshold, the determination module may be configured to map $I_{BPH}(29)$ to the intensity signal at the time frame $t_{30}$ of the processed ultrasound intensity signal (e.g., $I_{BPH}(29:30)$ at $t_{30}$). Accordingly, the computing system 120 may increase the portions between $t_{28}$ and $t_{29}$ of the obtained ultrasound signal that increase over the threshold, and may flatten the portions between $t_{29}$ and $t_{30}$ of the obtained ultrasound signal that does not increase over the threshold, such that the time intensity curves in the diagram 310 may convert to the monotonically increasing curve in diagram 410, as shown in FIG. 4A.

Referring back to FIG. 2, the generating module 206 may be configured to generate a sequence of images of the region of interest based at least on the processed time-dependent ultrasound signal of the each location. In some embodiments, the generated sequence of images may display signal variations of the processed time-dependent ultrasound signal in one or more structures in the region of interest to render the one or more structures. The one or more structures may refer to vascular structures, such as blood vessels. The sequence of images may be an contrast enhanced ultrasound quantification imaging video sequence in a series of time frames that may display dynamic information of vascular structures in the ROI. For example, the sequence of images may display vascular flow and perfusion imaging with ultrasound contrast agents within the ROI. The ROI may comprise a plurality of blood vessels, and the vascular flow and perfusion of the contrast agent as carried by blood in the different blood vessels may be affected by the vessels sizes, distance from the injection spot, etc. The generated sequence of images are illustrated in FIG. 4B.

Figure 4B:
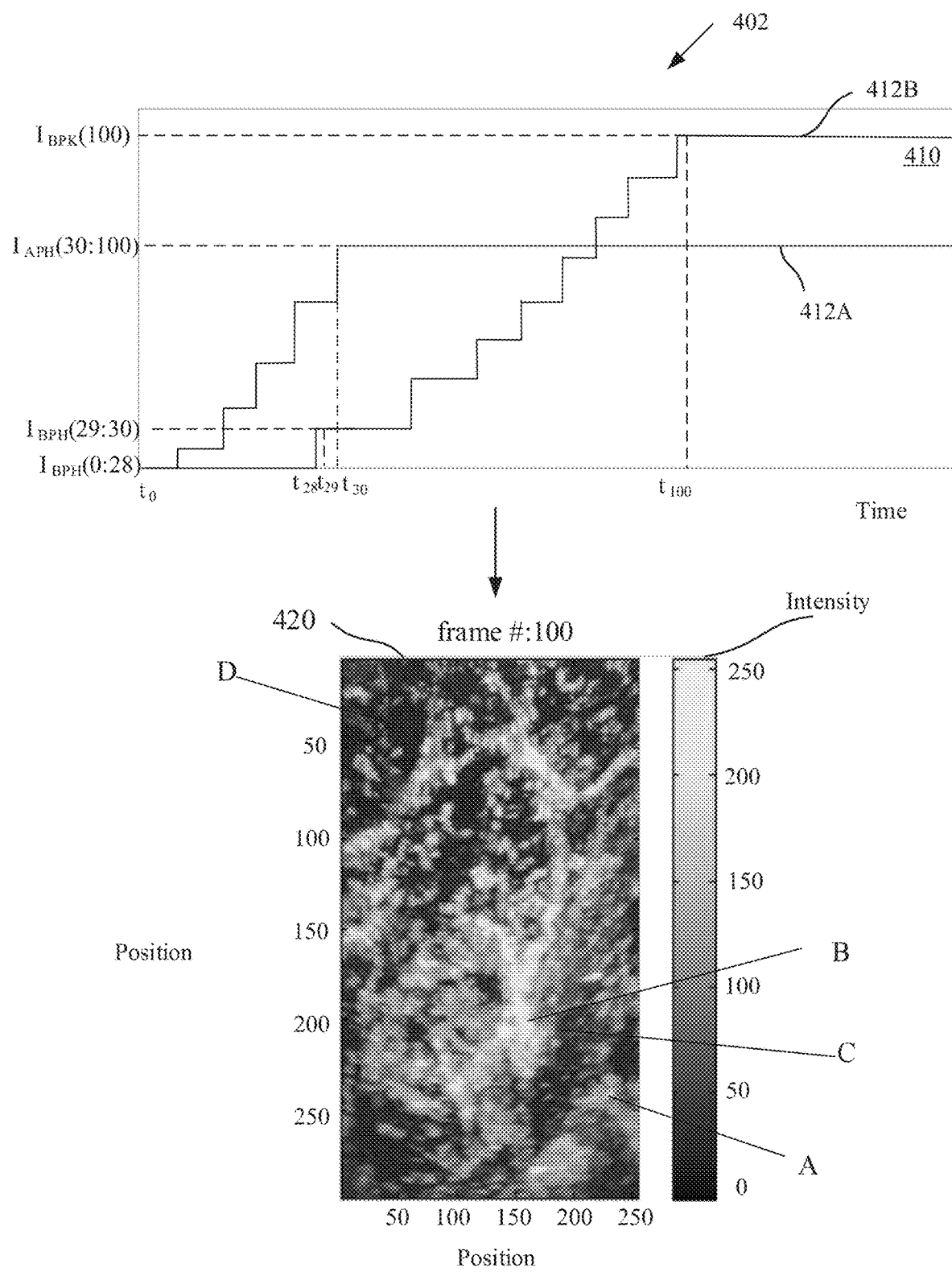

Referring to FIG. 4B, FIG. 4B illustrates workflow of the generating module 206, in accordance with various embodiments. In some embodiments, the generating module 206 may be configured to generate a sequence of images based on the processed ultrasound signal of the each locations at each time frame in the series of time frames. Each image may show the ROI in two dimensions (e.g., x-y coordinates) for indicating relative positions. For example, one or more pixels of the image 404 may correspond to a location in the ROI. The image 420 shows the processed ultrasound intensity signals in the ROI at the time frame $t_{100}$. According to the diagram 410, the processed ultrasound intensity signal of the location A at the time frame $t_{100}$ may be $I_{APH}(30:100)$, and the processed ultrasound intensity signal of the location B at the time frame $t_{100}$ may be $I_{BPH}(100)$. Since the processed ultrasound intensity signal may be always increasing or remain constant (e.g., see 412A and 412B), the generated sequence of images may display an increasing intensity signal of the each location within the time frame. For example, in the generated sequence between $t_0$ to $t_{100}$, the image 420 at the time frame $t_{100}$ may display the each location's peak value (i.e. maximum intensity signal) in the ROI based on the determined processed ultrasound signal of the each locations. The peak value may be the highest intensity signal of the TIC. That is, when the intensity signal, at the each location in the ROI, stops increasing or remains unchanged, the intensity signal reaches the peak value of the each location. In some embodiments, the intensity signals of different locations may reach its peak value at different time frames. For example, as shown in FIG. 4A, at the location A, the signal intensity reaches its peak value at the time frame $t_{30}$ (i.e., $I_A(30)$), and at the location B, the signal intensity reaches its peak value at the time frame $t_{100}$ (i.e., $I_B(100)$). In such situation, the system may hold the peak value of the ultrasound signal (i.e. the maximum intensity signal) at the location A from the time frame $t_{30}$ to the ending time frame (e.g., $t_{100}$). The generating module 206 may be configured to generate a sequence of images including the maximum intensity signals (i.e. the peak value of the ultrasound signal) of all the locations in the ROI at the ending time frame (e.g., 420). In the sequence of images, at some locations which may have peak values arrive earlier than some other locations, the peak value of the some locations in the ROI may be held in the images. In some embodiments, the ending time frame may be determined to be the time frame when the intensity signals of all the locations in the ROI reach the peak value.

In some embodiments, the computing system 120 may be configured to determine one or more locations showing abnormality. In one embodiment, before generating the sequence of images, the computing system 120 may be configured to compare a predetermined time-dependent ultrasound signal and the processed time-dependent ultrasound signal, and to determine, based at least on the comparison, one or more locations showing abnormality. For example, the computing system 120 may compare the processed time-dependent ultrasound signal with baseline (e.g., predetermined ultrasound signal for a healthy body). For example, a predetermined time-dependent ultrasound signal of a first location in a ROI at a time frame $t_{50}$ may be determined to be $I_{PH}(50)$. If the processed time-dependent ultrasound signal of the same first location in the same ROI from a patient is determined to be $I_{PH}(30)$, the computing system 120 may determine abnormality at the first location. Alternatively, the computing system 120 may compare the generated sequence of images with a baseline sequence of images for a healthy body for the comparison. For example, if the generated sequence of images, in comparison with the baseline sequence of images, shows a slower wash-in process at a first location, the computing system 120 may determine abnormality at the first location, or around the first location (e.g., abnormality at somewhere between the injection spot and the first location). Based on either type of comparison, the computing system 120 may pinpoint on the generated image one or more locations (e.g., at the issue level) potentially causing health issues. In some embodiments, the generated sequence of images may comprise one or more labels indicating the one or more locations showing abnormality. The generating module 208 may then be configured to indicate the one or more locations showing abnormality on the generated sequence of images, by example, by labelling, highlighting, etc. The pinpointed location may be an indication of source for cancer cell, malignant tissue, vessel clog, etc.

In some embodiments, the generating module 206 may be configured to generate the sequence of images between a starting time frame and an ending time frame. The computing system may be configured to obtain the starting time frame and the ending time frame. With the starting and ending time frame, the computing system 120 may obtain the processed time-dependent ultrasound signal for the locations in the ROI from the starting time frame until the ending time frame to improve efficiency and optimize storage. In some embodiments, the computing system may be configured to determine the ending time frame to improve efficiency. For example, referring to diagram 410 in FIG. 4B, the processed ultrasound intensity signal for the locations A and B at the time frame $t_{100}$ is $I_{APH}(30:100)$ and $I_{BPH}(100)$, and at any time frame after the time frame $t_{100}$, the processed ultrasound intensity signal for both locations A and B remains the same, that is, remains $I_{APH}(30:100)$ and $I_{BPH}(100)$. In such situation, the computing system 120 may be configured to determine $t_{100}$ to be the ending time frame, and stop processing at the time frame $t_{100}$.

In some embodiments, the sequence of images may be changed based on an update of the a starting time frame and an ending time frame, and the computing system 120 may adjust the generated sequence accordingly in real time. The computing system 120 may be configured to obtain an updated starting time frame and/or an updated ending time frame. The generated module 206 may be configured to correspondingly update the generated sequence of images based at least on the updated starting time frame and/or the updated ending time frame. For example, in the diagram 410 in FIG. 4B, the ending time frame $t_{100}$ may be original obtained ending time frame (i.e., before the update). By the update, the ending time frame may become $t_{30}$. For the location A, the ultrasound intensity signal at the ending time frame $t_{100}$ and the updated ending time $t_{30}$ is the same (i.e. $I_{APH}(30:100)$). Accordingly, the wash-in process of blood perfusion at the location A may be the same between the original and the updated ending time frame (i.e., $t_{30}$). As another example, for the location B, the ultrasound intensity signal at the original ending time frame $t_{100}$ is $I_{BPH}(100)$, and by the update, the intensity signal is $I_{BPH}(29:30)$ at the updated ending time frame $t_{30}$. Accordingly, the wash-in process of blood perfusion at the location B may be updated at the updated ending time frame (i.e., $t_{30}$).

In some embodiments, the computing system 120 may be configured to obtain a user-controllable display speed. The generating module 206 may be configured to display the generated sequence of images based at least on the obtained user-controllable display speed. For example, the computing system 120 may obtain, through the user interface, a display speed. The displayed sequence of images showing blood flow and perfusion within the ROI may be played by the obtained display speed.

The generated sequence may provide rich medical information, including blood flow distribution. In one embodiment, the generated sequence of images may display a wash-in process of agent-carrying blood perfusing through one or more vascular structures in the region of interest. The wash-in process may refer to a progressive enhancement within the ROI from the arrival of the contrast agent to peak enhancement. The generated sequence of images may display the wash-in process for the each location, and retain visualization of vascular perfusion of different blood vessels in the ROI. In some embodiments, the wash-in process of two nearby locations may indicate that the two locations correspond to different biological parts, such as two locally different blood vessels. For example, as shown in the image 420 in FIG. 4B, the ultrasound intensity signal may be higher in the location B than in the nearby location C at the same time frame (e.g., $t_{100}$). That is, the location B may indicate a faster reception of the contrast agent and render structure of artery in the ROI, while the location C may indicate a later reception of the contrast agent and renders a structure of capillary in the ROI based on the wash-in process. The vast background of the image (e.g., location D) may indicate tissue regions that are the slowest to receive the contrast agent. Thus, different organic structures inside the body may be visualized by different wash-in processes of the contrast agent. Based on the displayed wash-in processes of different locations, the computing system 120 may measure relative blood velocities in different vascular structures.

In some embodiments, the generated sequence of images may provide blood perfusion and vascular structure information. The perfusion of the contrast agent as carried by blood in different blood vessels may be affected by the vessel size, distance from the injection spot, etc. In some embodiments, the ROI may comprise a plurality of blood vessels of different sizes, and different contrast enhancements (e.g., wash-in processes) of the processed ultrasound intensity signal may indicate relative blood flow velocities in the plurality of blood vessels. For example, if the wash-in process of the location B is faster than the wash-in process of the location C, the blood flow velocities at the location B may be faster than that at the location C. That is, according to the generated sequence, the artery around the location B appears to receive the contrast agent faster than the capillary around the location C. As another example, if the processed intensity signal at the ending time frame of the location B is higher than that of the location A, the size of the blood vessel at the location B may be larger than that at the location A.

Figure 5:
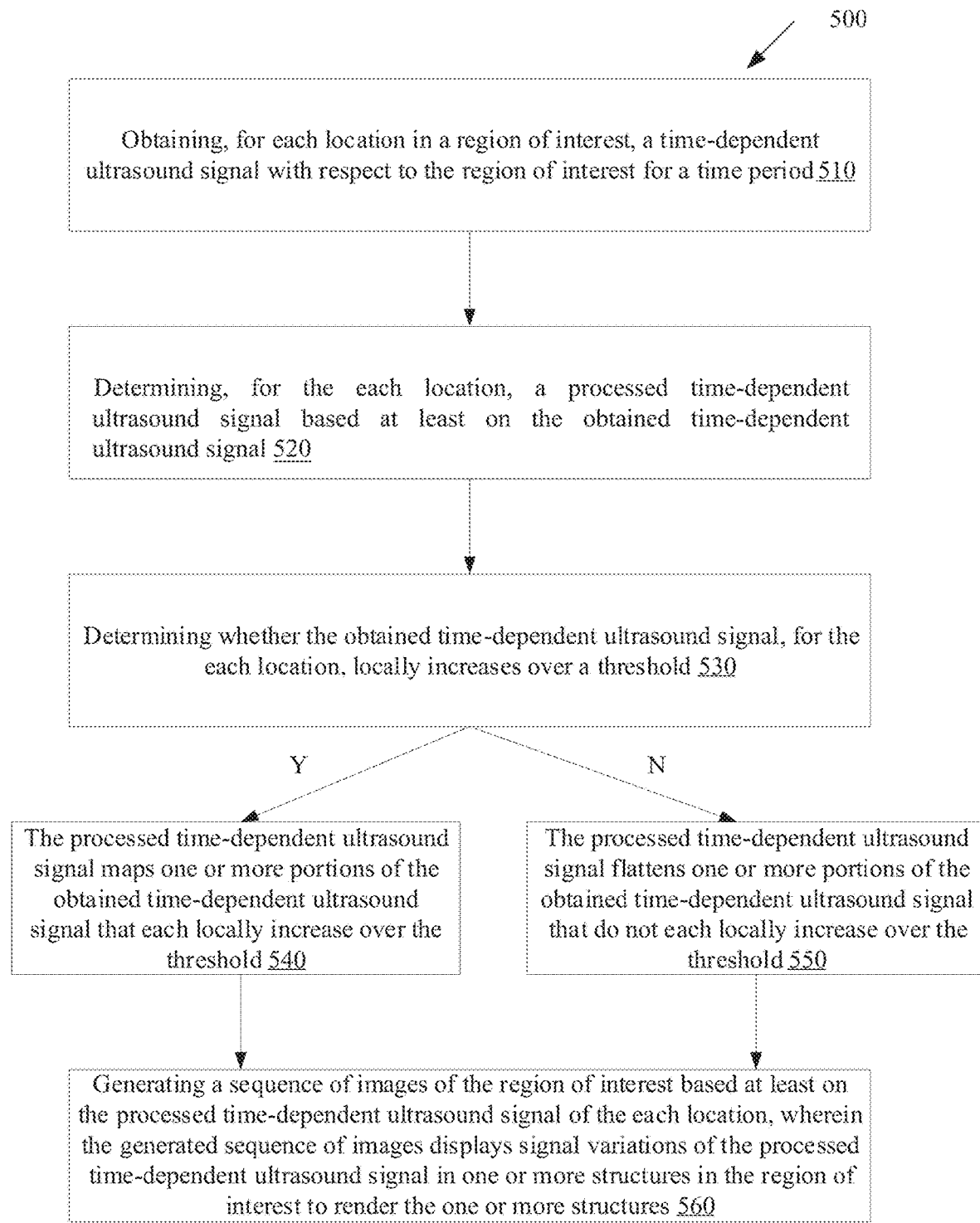
FIG. 5 depicts a flowchart of an exemplary method for contrast enhanced ultrasound quantification imaging, in accordance with various embodiments.

FIG. 5 illustrates a flowchart of an exemplary method 500, according to various embodiments of the present disclosure. The method 500 may be performed by one or more components of the CEUS QI system 100, such as the computing system 120. The operations of the method 500 presented below are intended to be illustrative. Depending on the implementation, the method 500 may include additional, fewer, or alternative steps performed in various orders or in parallel.

Block 510 comprises obtaining, for each location in a region of interest, a time-dependent ultrasound signal with respect to the region of interest for a time period. Block 520 comprises determining, for the each location, a processed time-dependent ultrasound signal based at least on the obtained time-dependent ultrasound signal. Block 530 comprises determining whether the obtained time-dependent ultrasound signal, for the each location, locally increases over a threshold, wherein in block 540, the processed time-dependent ultrasound signal maps one or more portions of the obtained time-dependent ultrasound signal that each locally increase over the threshold, and in block 550, the processed time-dependent ultrasound signal flattens one or more portions of the obtained time-dependent ultrasound signal that do not each locally increase over the threshold. Block 560 comprises generating a sequence of images of the region of interest based at least on the processed time-dependent ultrasound signal of the each location, wherein the generated sequence of images displays signal variations of the processed time-dependent ultrasound signal in one or more structures in the region of interest to render the one or more structures.

In some embodiments, the generated sequence of images display a wash-in process of agent-carrying blood perfusing through a cross section of the one or more vascular structures in the region of interest.

In some embodiments, the obtained time-dependent ultrasound signal comprises an obtained ultrasound intensity signal in a series of time frames from a first to a last time frame according to progression of time; and the processed time-dependent ultrasound signal comprises a processed ultrasound intensity signal in the series of time frames.

In some embodiments, determining a processed time-dependent ultrasound signal based at least on the obtained time-dependent ultrasound signal comprises: for the first time frame, mapping the obtained time-dependent ultrasound intensity signal to the processed time-dependent intensity ultrasound signal; and consecutively for each of the series of time frames after the first time frame: determining whether a current ultrasound intensity signal in a current time frame of the obtained time-dependent ultrasound intensity signal exceeds a previous ultrasound intensity signal in a previous time frame of the processed time-dependent ultrasound intensity signal for over the threshold, mapping, in response to the current ultrasound intensity signal exceeding the previous ultrasound intensity signal for over the threshold, the current ultrasound intensity signal in the current time frame of the obtained time-dependent ultrasound intensity signal to a current intensity signal in the current time frame of the processed time-dependent ultrasound intensity, and mapping, in response to the current ultrasound intensity signal not exceeding the previous ultrasound intensity signal for over the threshold, the previous ultrasound intensity signal in the previous time frame of the processed time-dependent ultrasound intensity signal for over the threshold to the current intensity signal in the current time frame of the processed time-dependent ultrasound intensity signal.

In some embodiments, generating the sequence of images of the region of interest based at least on the processed time-dependent ultrasound signal of the each location comprises: obtaining a starting time frame and an ending time frame; and generating the sequence of images between the starting time frame and the ending time frame.

Figure 6:
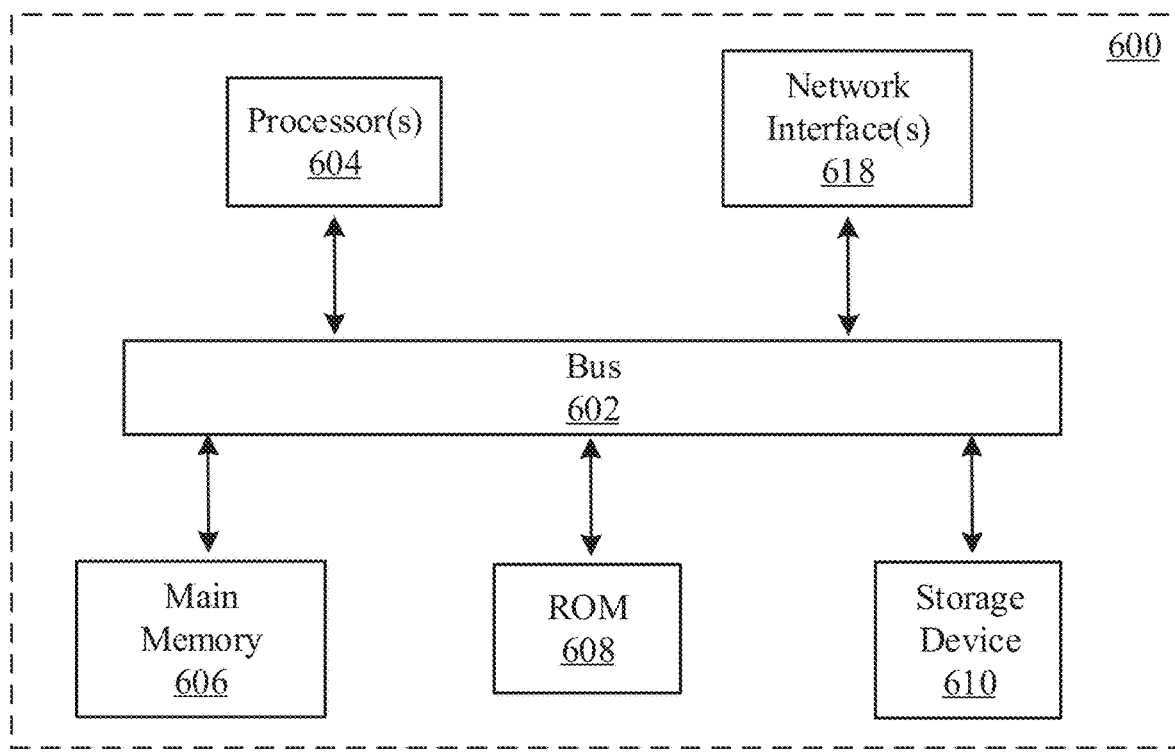
FIG. 6 is a block diagram that illustrates a computer system upon which any of the embodiments described herein may be implemented.

FIG. 6 is a block diagram that illustrates a computer system 600 upon which any of the embodiments described herein may be implemented. The computer system 600 may be implemented in any of the components of the devices, apparatuses, or systems illustrated in FIGS. 1-5. For example, the computing system 120 may implement the computer system 600. One or more of the methods described with reference to FIGS. 1-5, such as the method 500, may be performed by one or more implementations of the computer system 600. The computer system 600 includes a bus 602 or other communication mechanism for communicating information, one or more hardware processors 604 coupled with bus 602 for processing information. Hardware processor(s) 604 may be, for example, one or more general purpose microprocessors.

The computer system 600 may include a bus 602 or other communication mechanism for communicating information, one or more hardware processor(s) 604 coupled with bus 602 for processing information. Hardware processor(s) 604 may be, for example, one or more general purpose microprocessors.

The computer system 600 may also include a main memory 606, such as a random-access memory (RAM), cache and/or other dynamic storage devices, coupled to bus 602 for storing information and instructions executable by processor(s) 604. Main memory 606 also may be used for storing temporary variables or other intermediate information during execution of instructions executable by processor(s) 604. Such instructions, when stored in storage media accessible to processor(s) 604, render computer system 600 into a special-purpose machine that is customized to perform the operations specified in the instructions. The computer system 600 may further include a read only memory (ROM) 608 or other static storage device coupled to bus 602 for storing static information and instructions for processor(s) 604. A storage device 610, such as a magnetic disk, optical disk, or USB thumb drive (Flash drive), etc., may be provided and coupled to bus 602 for storing information and instructions.

The computer system 600 may implement the techniques described herein using customized hard-wired logic, one or more ASICs or FPGAs, firmware and/or program logic which in combination with the computer system causes or programs computer system 600 to be a special-purpose machine. According to one embodiment, the operations, methods, and processes described herein are performed by computer system 600 in response to processor(s) 604 executing one or more sequences of one or more instructions contained in main memory 606. Such instructions may be read into main memory 606 from another storage medium, such as storage device 610. Execution of the sequences of instructions contained in main memory 606 may cause processor(s) 604 to perform the process steps described herein. In alternative embodiments, hard-wired circuitry may be used in place of or in combination with software instructions.

The main memory 606, the ROM 608, and/or the storage device 610 may include non-transitory storage media. The term "non-transitory media," and similar terms, as used herein refers to media that store data and/or instructions that cause a machine to operate in a specific fashion, the media excludes transitory signals. Such non-transitory media may comprise non-volatile media and/or volatile media. Non-volatile media includes, for example, optical or magnetic disks, such as storage device 610. Volatile media includes dynamic memory, such as main memory 606. Common forms of non-transitory media include, for example, a floppy disk, a flexible disk, hard disk, solid state drive, magnetic tape, or any other magnetic data storage medium, a CD-ROM, any other optical data storage medium, any physical medium with patterns of holes, a RAM, a PROM, and EPROM, a FLASH-EPROM, NVRAM, any other memory chip or cartridge, and networked versions of the same.

The computer system 600 may include a network interface 618 coupled to bus 602. Network interface 618 may provide a two-way data communication coupling to one or more network links that are connected to one or more local networks. For example, network interface 618 may be an integrated services digital network (ISDN) card, cable modem, satellite modem, or a modem to provide a data communication connection to a corresponding type of telephone line. As another example, network interface 618 may be a local area network (LAN) card to provide a data communication connection to a compatible LAN (or WAN component to communicated with a WAN). Wireless links may also be implemented. In any such implementation, network interface 618 may send and receive electrical, electromagnetic or optical signals that carry digital data streams representing various types of information.

The computer system 600 can send messages and receive data, including program code, through the network(s), network link and network interface 618. In the Internet example, a server might transmit a requested code for an application program through the Internet, the ISP, the local network and the network interface 618.

The received code may be executed by processor(s) 604 as it is received, and/or stored in storage device 610, or other non-volatile storage for later execution.

Each of the processes, methods, and algorithms described in the preceding sections may be embodied in, and fully or partially automated by, code modules executed by one or more computer systems or computer processors comprising computer hardware. The processes and algorithms may be implemented partially or wholly in application-specific circuitry.

The various features and processes described above may be used independently of one another or may be combined in various ways. All possible combinations and sub-combinations are intended to fall within the scope of this specification. In addition, certain method or process blocks may be omitted in some implementations. The methods and processes described herein are also not limited to any particular sequence, and the blocks or states relating thereto can be performed in other sequences that are appropriate. For example, described blocks or states may be performed in an order other than that specifically disclosed, or multiple blocks or states may be combined in a single block or state. The examples of blocks or states may be performed in serial, in parallel, or in some other manner. Blocks or states may be added to or removed from the disclosed embodiments. The examples of systems and components described herein may be configured differently than described. For example, elements may be added to, removed from, or rearranged compared to the disclosed embodiments.

The various operations of methods described herein may be performed, at least partially, by one or more processors that are temporarily configured (e.g., by software) or permanently configured to perform the relevant operations. Whether temporarily or permanently configured, such processors may constitute processor-implemented engines that operate to perform one or more operations or functions described herein.

Similarly, the methods described herein may be at least partially processor-implemented, with a particular processor or processors being an example of hardware. For example, at least some of the operations of a method may be performed by one or more processors or processor-implemented engines. Moreover, the one or more processors may also operate to support performance of the relevant operations in a "cloud computing" environment or as a "software as a service" (SaaS). For example, at least some of the operations may be performed by a group of computers (as examples of machines including processors), with these operations being accessible via a network (e.g., the Internet) and via one or more appropriate interfaces (e.g., an Application Program Interface (API)).

The performance of certain of the operations may be distributed among the processors, not only residing within a single machine, but deployed across a number of machines. In some embodiments, the processors or processor-implemented engines may be located in a single geographic location (e.g., within a home environment, an office environment, or a server farm). In other embodiments, the processors or processor-implemented engines may be distributed across a number of geographic locations.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in configurations may be implemented as a combined structure or component. Similarly, structures and functionality presented as a single component may be implemented as separate components. These and other variations, modifications, additions, and improvements fall within the scope of the subject matter herein.

Although an overview of the subject matter has been described with reference to specific embodiments, various modifications and changes may be made to these embodiments without departing from the broader scope of embodiments of the specification. The Detailed Description should not to be taken in a limiting sense, and the scope of various embodiments is defined only by the appended claims, along with the full range of equivalents to which such claims are entitled. Furthermore, related terms (such as "first," "second," "third," etc.) used herein do not denote any order, height, or importance, but rather are used to distinguish one element from another element. Furthermore, the terms "a," "an," and "plurality" do not denote a limitation of quantity herein, but rather denote the presence of at least one of the articles mentioned.

What is claimed is:

1. A method for contrast enhanced ultrasound quantification imaging, comprising:
    obtaining, for each location in a region of interest, a time-dependent ultrasound signal with respect to the region of interest for a time period including a series of time points from a first time point to a last time point;
    determining, for each location, a processed time-dependent ultrasound signal based at least on the obtained time-dependent ultrasound signal and a threshold, by:
        for the first time point, assigning an intensity of the obtained time-dependent ultrasound signal at the first time point to an intensity of the processed time-dependent ultrasound signal at the first time point; and
        for each time point of the series of time points after the first time point:
            determining whether an increment between the intensity of the obtained time-dependent ultrasound signal at a current time point and the intensity of the processed time-dependent ultrasound signal at a previous time point exceeds the threshold, wherein the previous time point is a time point immediately before the current time point,
            in response to determining that the increment exceeds the threshold, assigning the intensity of the obtained time-dependent ultrasound signal at the current time point to the intensity of the processed time-dependent ultrasound signal at the current time point, and
            in response to determining that the increment does not exceed the threshold when the intensity of the obtained time-dependent ultrasound signal at the current time point is greater than the intensity of the processed time-dependent ultrasound signal at the previous time point, assigning the intensity of the processed time-dependent ultrasound signal at the previous time point to the intensity of the processed time-dependent ultrasound signal at the current time point; and
    generating a sequence of images of the region of interest based at least on the processed time-dependent ultrasound signal of each location, wherein the generated sequence of images displays signal variations of the processed time-dependent ultrasound signal in one or more vascular structures in the region of interest to render the one or more vascular structures.

2. The method of claim 1, wherein the generated sequence of images display a wash-in process of agent-carrying blood perfusing through a cross section of the one or more vascular structures in the region of interest.

3. The method of claim 1, wherein generating the sequence of images of the region of interest based at least on the processed time-dependent ultrasound signal of each location comprises:
    obtaining the first time point and the last time point; and
    generating the sequence of images between the first time point and the last time point.

4. The method of claim 1, wherein a time period between the current time point and the previous time point constitutes a time frame.

5. A non-transitory computer-readable storage medium configured with instructions executable by one or more processors to cause the one or more processors to perform contrast enhanced ultrasound quantification imaging operations comprising:
    obtaining, for each location in a region of interest, a time-dependent ultrasound signal with respect to the region of interest for a time period including a series of time points from a first time point to a last time point;
    determining, for each location, a processed time-dependent ultrasound signal based at least on the obtained time-dependent ultrasound signal and a threshold, by:
    for the first time point, assigning an intensity of the obtained time-dependent ultrasound signal at the first time point to an intensity of the processed time-dependent ultrasound signal at the first time point; and
    for each time point of the series of time points after the first time point:
        determining whether an increment between the intensity of the obtained time-dependent ultrasound signal at a current time point and the intensity of the processed time-dependent ultrasound signal at a previous time point exceeds the threshold, wherein the previous time point is a time point immediately before the current time point, in response to determining that the increment exceeds the threshold, assigning the intensity of the obtained time-dependent ultrasound signal at the current time point to the intensity of the processed time-dependent ultrasound signal at the current time point, and in response to determining that the increment does not exceed the threshold when the intensity of the obtained time-dependent ultrasound signal at the current time point is greater than the intensity of the processed time-dependent ultrasound signal at the previous time point, assigning the intensity of the processed time-dependent ultrasound signal at the previous time point to the intensity of the processed time-dependent ultrasound signal at the current time point; and generating a sequence of images of the region of interest based at least on the processed time-dependent ultrasound signal of each location, wherein the generated sequence of images displays signal variations of the processed time-dependent ultrasound signal in one or more vascular structures in the region of interest to render the one or more vascular structures.

6. The non-transitory computer-readable storage medium of claim 5, wherein the generated sequence of images display a wash-in process of agent-carrying blood perfusing through the one or more vascular structures in the region of interest.

7. The non-transitory computer-readable storage medium of claim 5, wherein the processed time-dependent ultrasound signal is a monotonically increasing signal.

8. The non-transitory computer-readable storage medium of claim 5, wherein generating the sequence of images of the region of interest based at least on the processed time-dependent ultrasound signal of each location comprises:
obtaining the first time point and the last time point; and
generating the sequence of images between the first time point and the last time point.

9. The non-transitory computer-readable storage medium of claim 8, wherein the operations further comprise:
obtaining an updated starting time point or an updated ending time point; and
correspondingly updating the generated sequence of images based at least on the updated starting time point or the updated ending time point.

10. The non-transitory computer-readable storage medium of claim 5, wherein the operations further comprise:
obtaining a user-controllable display speed; and
displaying the generated sequence of images based at least on the obtained user-controllable display speed.

11. The non-transitory computer-readable storage medium of claim 5, wherein, before generating the sequence of images, the operations further comprise:
comparing a predetermined time-dependent ultrasound signal and the processed time-dependent ultrasound signal; and
determining, based at least on the comparison, one or more locations showing abnormality, wherein:
the generated sequence of images comprise one or more labels indicating the one or more locations showing abnormality.

12. The non-transitory computer-readable storage medium of claim 5, wherein a time period between the current time point and the previous time point constitutes a time frame.

13. A device, comprising a memory and a processor, the memory comprising instructions executable by the processor to cause the processor to perform contrast enhanced ultrasound quantification imaging operations comprising:
obtaining, for each location in a region of interest, a time-dependent ultrasound signal with respect to the region of interest for a time period including a series of time points from a first time point to a last time point;
determining, for each location, a processed time-dependent ultrasound signal based at least on the obtained time-dependent ultrasound signal and a threshold, by:
for the first time point, assigning an intensity of the obtained time-dependent ultrasound signal at the first time point to an intensity of the processed time-dependent ultrasound signal at the first time point; and
for each time point of the series of time points after the first time point:
determining whether an increment between the intensity of the obtained time-dependent ultrasound signal at a current time point and the intensity of the processed time-dependent ultrasound signal at a previous time point exceeds the threshold, wherein the previous time point is a time point immediately before the current time point,
in response to determining that the increment exceeds the threshold, assigning the intensity of the obtained time-dependent ultrasound signal at the current time point to the intensity of the processed time-dependent ultrasound signal at the current time point, and
in response to determining that the increment does not exceed the threshold when the intensity of the obtained time-dependent ultrasound signal at the current time point is greater than the intensity of the processed time-dependent ultrasound signal at the previous time point, assigning the intensity of the processed time-dependent ultrasound signal at the previous time point to the intensity of the processed time-dependent ultrasound signal at the current time point; and
generating a sequence of images of the region of interest based at least on the processed time-dependent ultrasound signal of each location, wherein the generated sequence of images displays signal variations of the processed time-dependent ultrasound signal in one or more vascular structures in the region of interest to render the one or more vascular structures.

14. The device of claim 13, wherein the generated sequence of images display a wash-in process of agent-carrying blood perfusing through the one or more vascular structures in the region of interest.

15. The device of claim 13, wherein the processed time-dependent ultrasound signal is a monotonically increasing signal.

16. The device of claim 13, wherein generating the sequence of images of the region of interest based at least on the processed time-dependent ultrasound signal of each location comprises:
obtaining the first time point and the last time point; and
generating the sequence of images between the first time point and the last time point.

17. The device of claim 13, wherein the operations further comprise:
obtaining an updated first time point or an updated last time point; and correspondingly updating the generated sequence of images based at least on the updated first time point or the updated last time point.

18. The device of claim 13, wherein the operations further comprise:
obtaining a user-controllable display speed; and
displaying the generated sequence of images based at least on the obtained user-controllable display speed.

19. The device of claim 13, wherein, before generating the sequence of images, the operations further comprise:
comparing a predetermined time-dependent ultrasound signal and the processed time-dependent ultrasound signal; and
determining, based at least on the comparison, one or more locations showing abnormality, wherein:
the generated sequence of images comprise one or more labels indicating the one or more locations showing abnormality.

20. The device of claim 13, wherein a time period between the current time point and the previous time point constitutes a time frame.

\* \* \* \* \*